US 6,692,513 B2

(12) United States Patent
Streeter et al.

(10) Patent No.: US 6,692,513 B2
(45) Date of Patent: Feb. 17, 2004

(54) INTRAVASCULAR FILTER WITH DEBRIS ENTRAPMENT MECHANISM (75) Inventors: Richard B. Streeter, Winchester, MA (US); Gregory H. Lambrecht, Natick, MA (US); John R. Liddicoat, Sewickley, PA (US); Robert Kevin Moore, Natick, MA (US); Todd F. Davenport, Andover, MA (US)

(73) Assignee: Viacor, Inc., Wilmington, MA (US)

( * ) Notice: Subject to any disclaimer, the term of this patent is extended or adjusted under 35 U.S.C. 154(b) by 0 days.

(21) Appl. No.: 09/896,258

(22) Filed: Jun. 29, 2001

(65) Prior Publication Data
US 2002/0049468 A1 Apr. 25, 2002

Related U.S. Application Data
(60) Provisional application No. 60/231,101, filed on Sep. 8, 2000, and provisional application No. 60/215,542, filed on Jun. 30, 2000.

(51) Int. Cl.[7] .............................................. A61M 29/00
(52) U.S. Cl. ........................................................ 606/200
(58) Field of Search ................................. 606/200, 159, 606/108, 151, 194, 110; 604/96; 623/2.12, 2.14, 2.15, 2.16, 2.17, 2.18, 2.19

(56) References Cited

U.S. PATENT DOCUMENTS

| | | | | |
|---|---|---|---|---|
| 5,769,816 A | * | 6/1998 | Barbut et al. | 604/93.01 |
| 5,814,064 A | * | 9/1998 | Daniel et al. | 606/200 |
| 5,855,601 A | * | 1/1999 | Bessler et al. | 623/2.38 |

* cited by examiner

Primary Examiner—Vy Q. Bui
(74) Attorney, Agent, or Firm—Pandiscio & Pandiscio (57) ABSTRACT Apparatus for filtering and entrapping debris in the vascular system of a patient, the apparatus including a filter to allow blood to flow therethrough and to restrict passage of debris, wherein the filter captures debris carried in a first direction of blood flow. The apparatus further includes an entrapment mechanism which allows passage of debris and blood therethrough, in the first direction of blood flow and prevents debris passage in a second direction. The entrapment mechanism and filter allow blood and debris therethrough in the first direction of blood flow. The entrapment mechanism prevents debris flow in the second direction of blood flow A method for filtering and entrapping debris in the vascular system includes inserting the apparatus into the vascular system, allowing blood and debris carried therein to flow through the entrapment mechanism, and removing the apparatus and accumulated debris from the vascular system.

17 Claims, 8 Drawing Sheets

INTRAVASCULAR FILTER WITH DEBRIS ENTRAPMENT MECHANISM

REFERENCE TO PENDING PRIOR PATENT APPLICATION

This patent application claims benefit of prior U.S. Provisional Patent Application Ser. No. 60/215,542, filed Jun. 30, 2000 by Richard B. Streeter et al. for INTRAVASCULAR FILTER WITH DEBRIS ENTRAPMENT MECHANISM, which patent application is hereby incorporated herein by reference, and of prior U.S. Provisional Patent Application Ser. No. 60/231,101, filed Sep. 8, 2000 by Richard B. Streeter et al. for INTRAVASCULAR FILTER WITH DEBRIS ENTRAPMENT MECHANISM, which patent application is hereby incorporated herein by reference.

FIELD OF THE INVENTION

This invention relates to intravascular filtering apparatus and methods in general, and more particularly to apparatus and methods for filtering and irreversibly entrapping embolic debris from the vascular system during an intravascular or intracardiac procedure.

BACKGROUND OF THE INVENTION

Intracardiac and intravascular procedures, whether performed percutaneously or in an open, surgical, fashion, may liberate particulate debris. Such debris, once free in the vascular system, may cause complications including vascular occlusion, end-organ ischemia, stroke, and heart attack. Ideally, this debris is filtered from the vascular system before it can travel to distal organ beds.

Using known filter mechanisms deployed in the arterial system, debris is captured during systole. There is a danger, however, that such debris may escape the filter mechanism during diastole or during filter removal. Apparatus and methods to reduce debris escape during diastole or during filter removal may be desirable to reduce embolic complications.

SUMMARY OF THE INVENTION

An object of the invention is to provide a filtering mechanism that irreversibly entraps debris therein.

Another object of the invention is to provide a filtering mechanism that permanently captures debris from the intravascular system of a patient.

A further object of the invention is to provide a filtering mechanism with greater ability to collect debris in the intravascular system of a patient to decrease the number of complications attributable to such debris.

Another further object of this invention is to provide a filter holding mechanism suitable to be secured to a retractor used to create access to the heart and surrounding structures during heart surgery procedures.

A still further object is to provide a method for using a filtering mechanism in the intravascular system of a patient to permanently capture debris therefrom.

Another still further object of the present invention is to provide a method for introducing a filtering device in the aorta downstream of the aortic valve to restrict the passage of emboli while allowing blood to flow through the aorta during cardiovascular procedures, and to entrap debris collected in the filter so as to prevent its escape during cardiac diastole or during manipulation, repositioning or removal of the device from the aorta.

With the above and other objects in view, as will hereinafter appear, there is provided apparatus for debris removal from the vascular system of a patient, the apparatus comprising: a filtering device having a proximal side and a distal side, the filter being sized to allow blood flow therethrough and to restrict debris therethrough and the filter having a first given perimeter, wherein blood flow in a first direction passes from the proximal side to the distal side of the filtering device; an entrapment mechanism having a proximal side and a distal side, the entrapment mechanism forming a selective opening to allow debris and blood flow passage in the first direction from the proximal side to the distal side therethrough, the selective opening having a restriction mechanism to prevent debris passage in a second direction opposite to the first direction, the selective opening having a second given perimeter, the first given perimeter and the second given perimeter being deployed within the vascular system so as to form a chamber between the distal side of the entrapment mechanism and the proximal side of the filtering device, wherein the entrapment mechanism allows blood flow and debris to pass therethrough in the first direction, the filtering device allows blood flow to pass therethrough in the first direction, the restriction mechanism prevents debris from passing back through the selective opening in a second direction opposite to the first direction and the chamber contains the debris received through the entrapment mechanism so as to prevent the escape of the debris therein by the filtering device in the first direction and the restriction mechanism in the second direction.

In accordance with another further feature of the invention there is provided a method for filtering and entrapping debris from the vascular system of a patient, the method comprising: providing apparatus for filtering and entrapping debris from the vascular system of a patient, the apparatus comprising: a filter device being sized to allow blood flow therethrough and to restrict passage of debris therethrough, and the filter device having a first given perimeter, a proximal side and a distal side; and wherein the filtering device captures debris carried in a first direction of blood flow from the proximal side to the distal side thereof on the proximal side of the filter device; an entrapment mechanism having a proximal side and a distal side, the entrapment mechanism including a selective opening to allow passage of blood and debris therethrough, the selective opening being configured to allow passage of blood and debris carried therein therethrough in the first direction of blood flow from the proximal side to the distal side of the entrapment mechanism, the selective opening having a restriction mechanism to prevent debris passage from the distal side to the proximal side of the entrapment mechanism in a second direction opposite to the first direction, the selective opening forming a second given perimeter, and the first given perimeter and the second given perimeter being deployed witin the vascular system so as to form a chamber between the distal side of the entrapment mechanism and the proximal side of the filtering device; wherein the entrapment mechanism allows blood and debris carried therein therethrough in the first direction of blood flow, the filtering device allows blood therethrough in the first direction of blood flow, and the restriction mechanism prevents debris back through the selective opening in the second direction of blood flow opposite to the first direction of blood flow such that the chamber entraps the filtered debris received therein for debris removal from the vascular system of the patient; inserting the apparatus into the vascular system of the patient; allowing blood and debris carried therein to flow through the entrapment mechanism, and into the chamber; and removing the apparatus from the vascular system of the patient.

The above and other features of the invention, including various novel details of construction and combinations of parts and method steps will now be more particularly described with reference to the accompanying drawings and pointed out in the claims. It will be understood that the particular devices and method steps embodying the invention are shown by way of illustration only and not as limitations of the invention. The principles and features of this invention may be employed in various and numerous embodiments without departing from the scope of the invention.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein.

DETAILED DESCRIPTION OF THE PREFERRED EMBODIMENTS

A filtration and entrapment apparatus 5 is shown in FIGS. 1A–5D for debris removal from the vascular system of a patient. Filtration and entrapment apparatus 5 generally includes a filter device 10 and an entrapment mechanism 15. Filtration and entrapment apparatus 5 can be used to filter emboli during a variety of intravascular or intracardiac procedures, including, but not limited to, the following procedures: vascular diagnostic procedures, angioplasty, stenting, angioplasty and stenting, endovascular stent-graft and surgical procedures for aneurysm repairs, coronary artery bypass procedures, cardiac valve replacement and repair procedures, and carotid endardarectomy procedures.

Now looking at FIGS. 1A–1D, a preferred embodiment of the present invention is shown with filtration and entrapment apparatus 5 as described herein below.

Figure 1A:
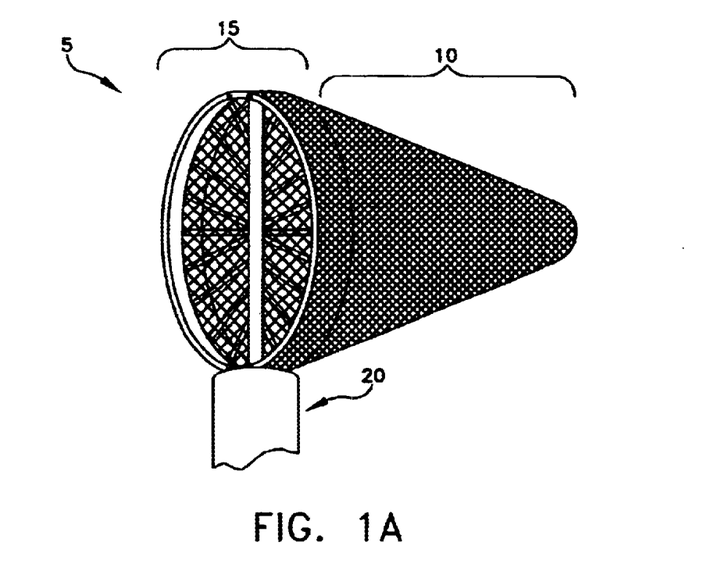
FIG. 1A is a perspective view of a deployable entrapment filtering device for debris removal showing the filtering device in its fully deployed shape as released from its cannula into the blood stream of a patient.

FIG. 1A depicts the profile of filtration and entrapment apparatus 5 in its fully deployed shape, with filter device 10 and entrapment mechanism 15 released from cannula 20 into the blood stream (not shown). Prior to deployment, filter device 10 and entrapment mechanism 15 are collapsed within cannula 20, e.g., by moving the proximal end 25A proximally along center post 50.

Figure 1B:
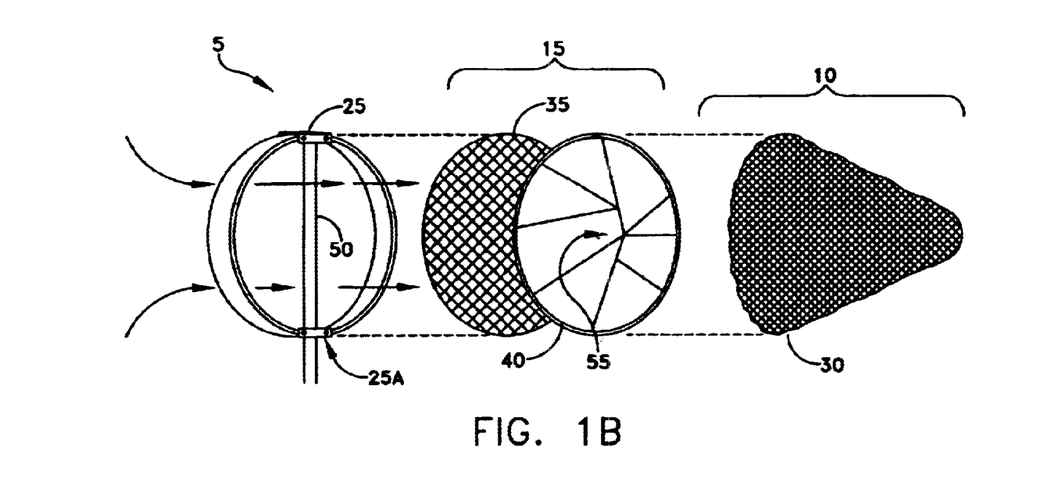
FIG. 1B is an exploded perspective view of the deployable entrapment filtering device of FIG. 1A showing the components thereof.

FIG. 1B depicts the primary components of filtration and entrapment apparatus 5 comprising filter device 10 and entrapment mechanism 15 in attachment to deployable frame 25. In the present embodiment of the invention, filter device 10 comprises a filter mesh bag 30, and entrapment mechanism 15 comprises a piece of coarse mesh 35 and a set of entrapment flaps 40.

Figure 1C:
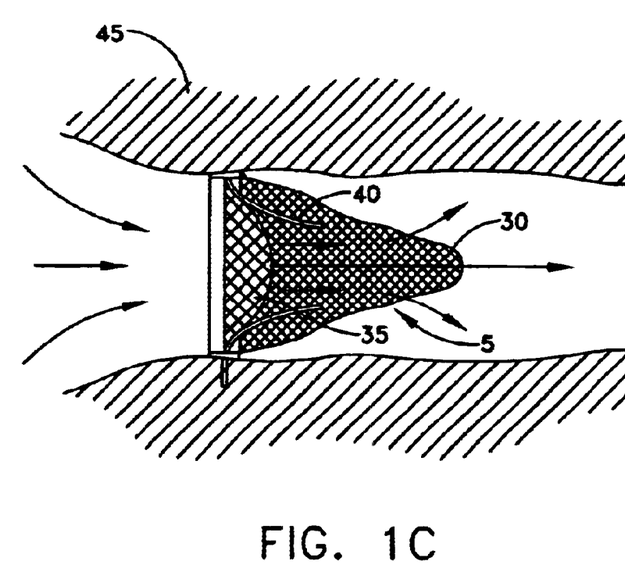
FIG. 1C is a schematic cross-sectional illustration depicting the deployable entrapment filtering device of FIGS. 1A and 1B during cardiac systole.

FIG. 1C depicts filtration and entrapment apparatus 5 deployed within an aorta 45 during cardiac systole. Blood and debris flow through opened deployable frame 25, across course mesh 35, between and through entrapment flaps 40 and into the end of the filter mesh bag 30. Entrapment flaps 40 ensure unidirectional flow of blood and debris into filter mesh bag 30.

Figure 1D:
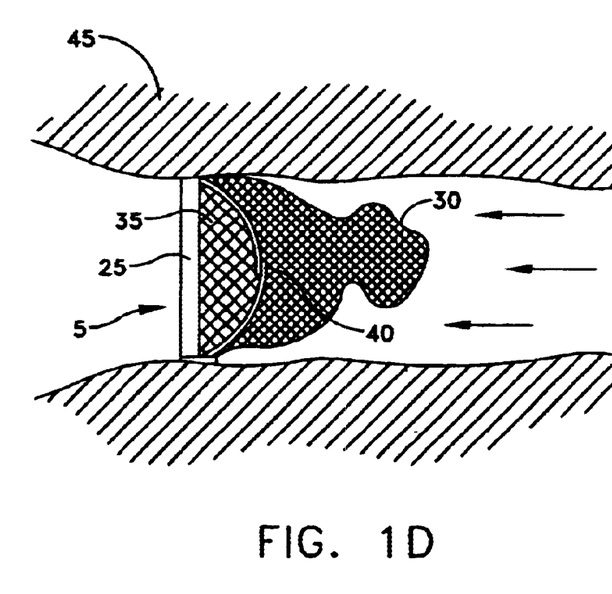
FIG. 1D is a schematic cross-sectional illustration depicting the deployable entrapment filtering device of FIGS. 1A and 1B during cardiac diastole.

FIG. 1D depicts filtration and entrapment apparatus 5 within the aorta 45 responding to any retrograde flow of blood and/or back pressure within the aorta 45 during cardiac diastole. The back flow of blood and/or back pressure causes filter mesh bag 30 to partially deform and entrapment flaps 40 to close against coarse mesh 35. Coarse mesh 35 is of a structure adequate to permit the free flow of blood and debris through it and into filter mesh bag 30, and serves as a supporting structure against which entrapment flaps 40 can close and remain in a closed position to prevent the escape of embolic debris.

Still looking at FIGS. 1A–1D, it should also be appreciated that the entrapment flaps 40 may be attached to structures other than deployable frame 25, e.g., the entrapment flaps 40 may be attached to center post 50, or to coarse mesh 35, etc. Furthermore, if desired, entrapment flaps 40 may be biased closed or biased open. In addition, entrapment mechanism 15 may consist of one or more flaps 55, and have a configuration including, but not limited to, a single disk diaphragm (not shown), a semi-lunar configuration (not shown), a gill slit configuration (not shown), a multi-leaflet flap configuration (not shown), etc.

It should also be appreciated that, while in the foregoing description the apparatus shown in FIGS. 1A–1D has been described in the context of functioning as a filter, it may also function as a one-way check valve. To the extent that the apparatus shown in FIGS. 1A–1D is intended to function primarily as a one-way check valve, filter mesh bag 30 (see FIG. 1B) may be retained or it may be omitted.

Figure 2A:
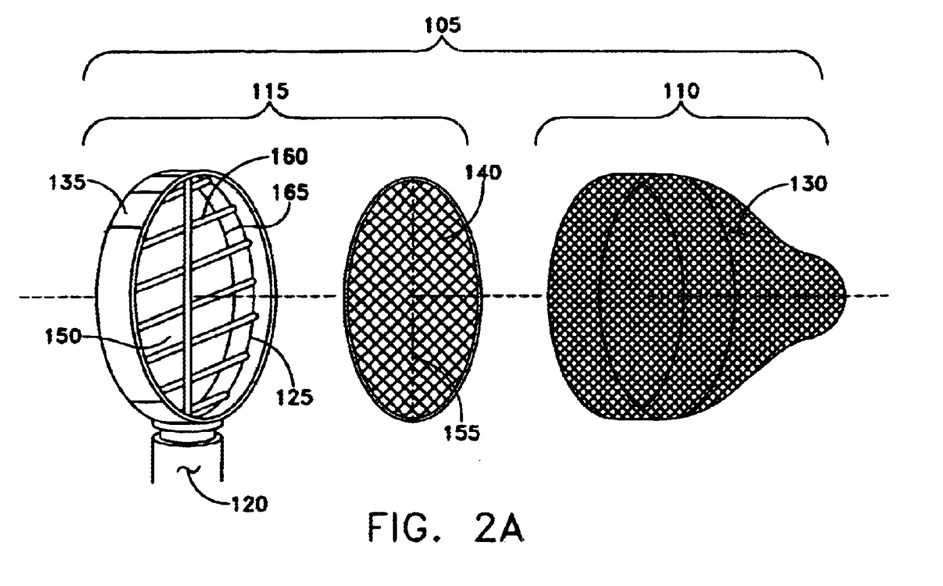
FIG. 2A is an exploded perspective view of a deployable entrapment filtering device for debris removal showing the components thereof including a set of filter mesh entrapment leaflets.
Figure 2B:
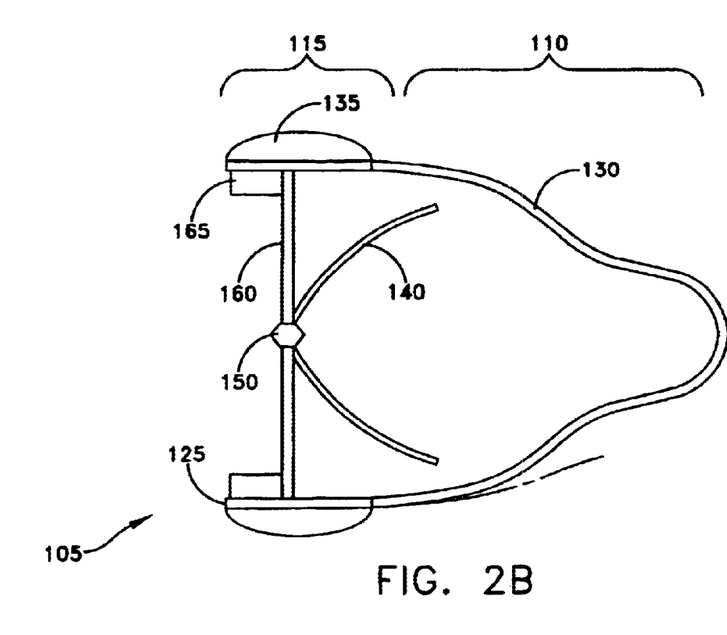
FIG. 2B is a schematic cross-sectional illustration depicting the deployable entrapment filtering device of FIG. 2A during cardiac systole.
Figure 3A:
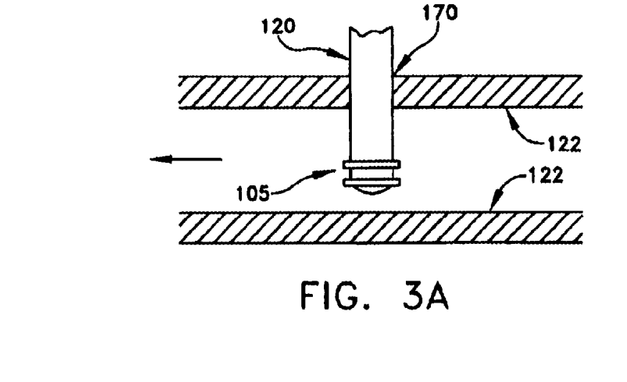
FIGS. 3A–3D are a series of schematic illustrations depicting a method of using the deployable entrapment filtering device of FIGS. 2A and 2B.
Figure 3B:
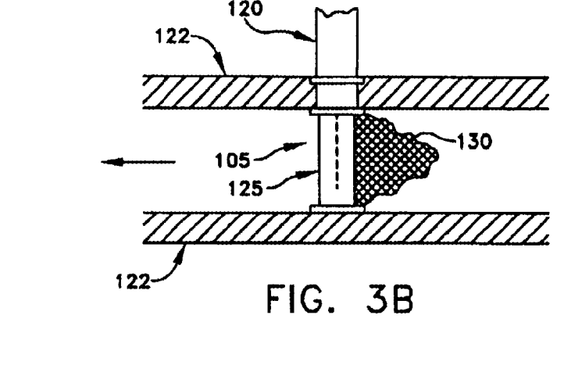
Figure 3C:
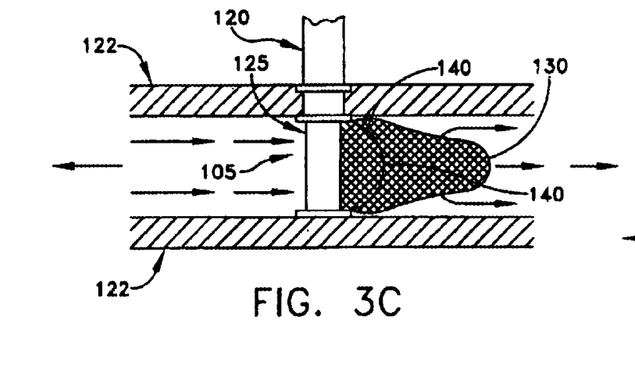
Figure 3D:
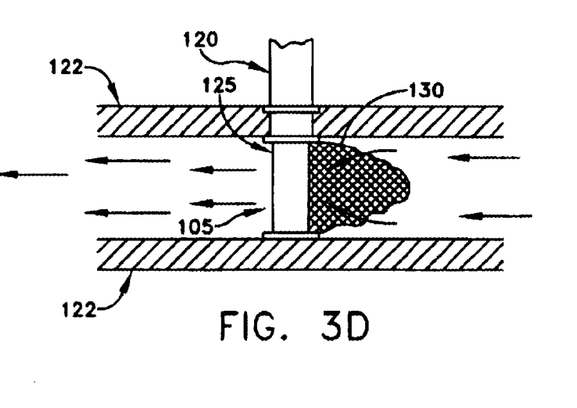

Looking next at FIGS. 2A and 2B, there is shown an alternative form of the present invention as a bidirectional flow filtration and entrapment apparatus 105. Bidirectional flow filtration and entrapment apparatus 105 of FIGS. 2A and 2B generally comprises a filter device 110 and an entrapment mechanism 115 delivered by a cannula 120 to the interior of a vascular structure 122 (see FIGS. 3A–3D); a deployable filter frame 125; a filter bag 130 attached to the perimeter of deployable filter frame 125; a compliant, soft outer cuff 135 (preferably formed out of a biologically inert material such as Teflon, Dacron, Silastic, etc.) for sealing filtration and entrapment apparatus 105 against the inner wall of vascular structure 122 when deployable filter frame 125 is expanded; entrapment leaflets 140, preferably in the form of a fine filter mesh; a center post 150 (preferably formed out of steel or the equivalent) passing across the interior of the deployable filter frame 125; a hinge line 155 on entrapment leaflets 140, connected to center post 150, for permitting the entrapment leaflets 140 to open and close; co-aptation strands 160 extending across the interior of deployable filter frame 125 and providing a seat against which entrapment leaflets 140 may close during diastole; and a perimeter seal 165 (preferably formed out of expanded Teflon or the like). Perimeter seal 165 acts like a step to help support entrapment leaflets 140 during diastole.

In addition, it should also be appreciated that soft outer cuff 135 may comprise a radially expandable mechanism (e.g., a balloon, a decompressed sponge, a spring loaded leaflet, etc.) for sealing filtration and entrapment apparatus 105 against the inner wall of vascular structure 122.

As noted above, entrapment leaflets 140 are preferably formed out of a fine filter mesh. This filter mesh is sized so that it will pass blood therethrough but not debris. Furthermore, this filter mesh is sized so that it will provide a modest resistance to blood flow, such that the entrapment leaflets will open during systole and close during diastole. By way of example but not limitation, the filter mesh may have a pore size of between about 40 microns and about 300 microns.

FIGS. 3A–3D illustrate operation or bidirectional flow filtration and entrapment apparatus 105 shown in FIGS. 2A and 2B. More particularly, cannula 120 of deployable filtration and entrapment apparatus 105 is first inserted through a small incision 170 in the wall of the vascular structure 122 (see FIG. 3A). Then deployable filter frame 125 is deployed (see FIG. 3B) Thereafter, during systole (see FIG. 3C), blood flows through deployable filter frame 125, forcing entrapment leaflets 140 open, and proceeds through filter bag 130. Any debris contained in the blood is captured by filter bag 130 and thereby prevented from moving downstream past bidirectional flow filtration and entrapment apparatus 105. During diastole (see FIG. 3D), when the blood flow momentarily reverses direction, entrapment leaflets 140 (shown in FIGS. 2A and 2B) close, seating against co-aptation strands 160 (shown in FIGS. 2A and 2B) extending across the interior of deployable filter frame 125 (shown in FIGS. 2A and 2B). The blood passes through the fine mesh of entrapment leaflets 140 (shown in FIGS. 2A and 2B), being filtered as it passes, thus permitting coronary profusion to take place during the diastolic phase. The fine mesh of entrapment leaflets 140 (shown in FIGS. 2A and 2B) prevents debris from passing back through bidirectional flow filtration and entrapment apparatus 105.

It should also be appreciated that with bidirectional flow filtration and entrapment apparatus 105 of FIGS. 2A, 2B and 3A–3D, entrapment leaflets 140 may be attached to structures other than center post 150, e.g., they may be attached to co-aptation strands 160, or to deployable filter frame 125, etc. Furthermore, if desired, entrapment leaflets 140 may be biased closed, or biased open. In addition, entrapment mechanism 115 may consist of one or more flaps (not shown), and have a configuration including, but not limited to, a single disk diaphragm (not shown), a semi-lunar configuration (not shown), a gill slit configuration (not shown), a multi-leaflet flap configuration (not shown), etc.

Figure 4A:
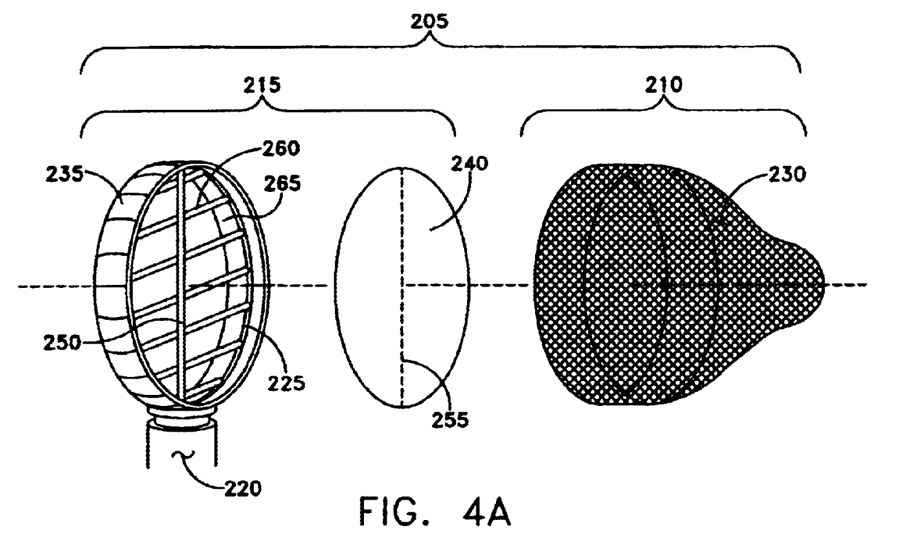
FIG. 4A is an exploded perspective view of a deployable entrapment filtering device for debris removal showing the components thereof including a set of non-porous valve leaflets.
Figure 4B:
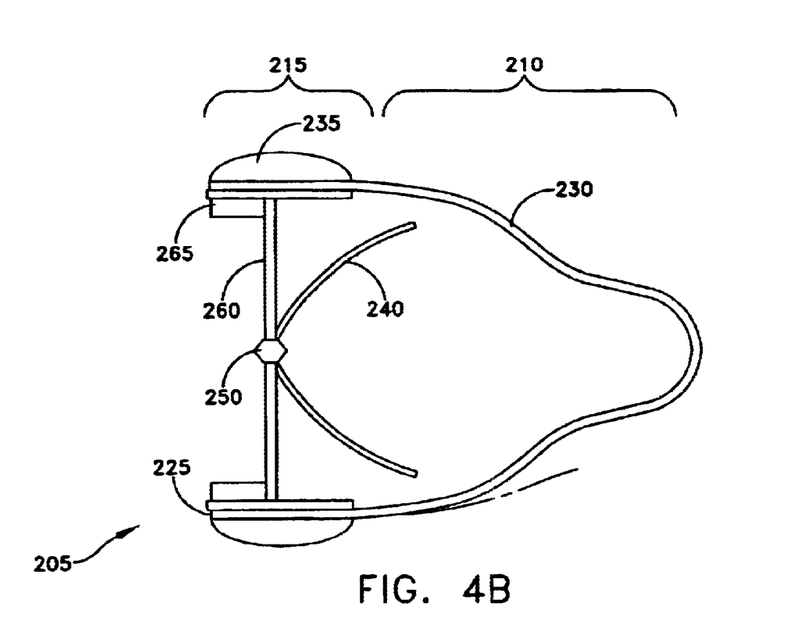
FIG. 4B is a schematic cross-sectional illustration depicting the deployable entrapment filtering device of FIG. 4A during cardiac systole.
Figure 5A:
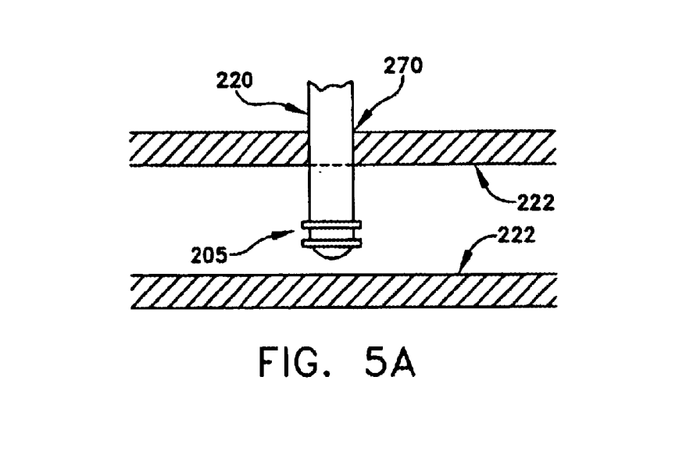
FIGS. 5A–5D are a series of schematic illustrations depicting a method of using the deployable entrapment filtering device of FIGS. 4A and 4B.
Figure 5B:
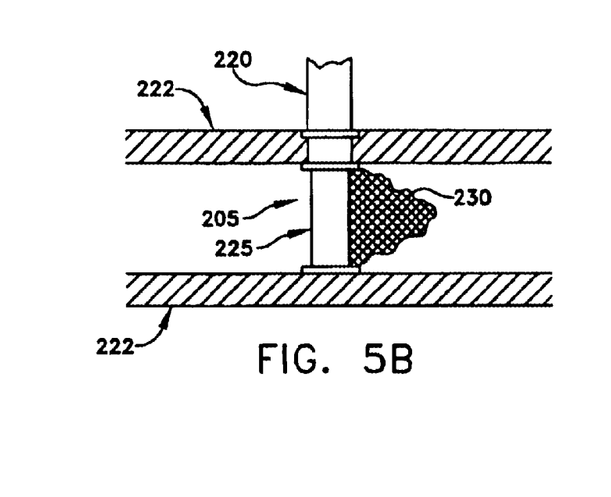
Figure 5C:
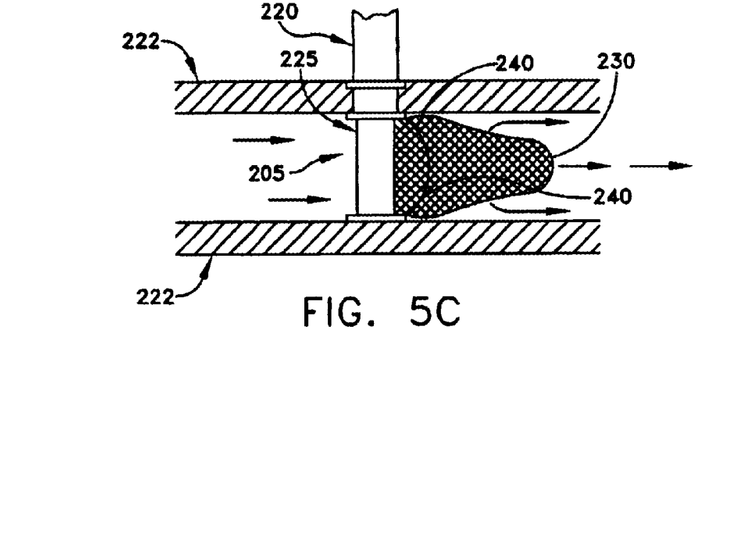
Figure 5D:
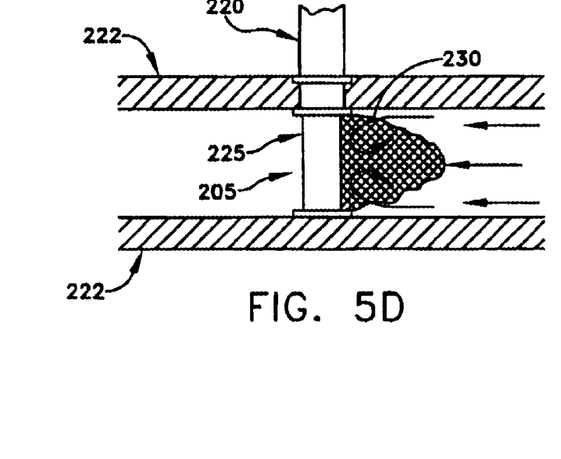

Looking next at FIGS. 4A and 4B, there is shown a deployable valve/filter apparatus 205. Deployable valve/filter apparatus 205 of FIGS. 4A and 4B generally comprises a filter device 210 and a valve entrapment mechanism 215 delivered by a cannula 220 to the interior of the vascular structure 222; a deployable valve/filter frame 225; a filter bag 230 attached to the perimeter of deployable valve/filter frame 225; a compliant, soft outer cuff 235 (preferably formed out of a biologically inert material such as Teflon, Dacron, Silastic, etc.) for sealing the filter device 210 against the inner wall of vascular structure 222 when deployable valve/filter frame 225 is expanded; valve leaflets 240, preferably in the form of a blood-impervious material; a center post 250 (preferably formed out of steel or the equivalent) passing across the interior of deployable valve/filter frame 225; a hinge line 255 on valve leaflets 240, connected to center post 250, for permitting valve leaflets 240 to open and close; co-aptation strands 260 extending across the interior of deployable valve/filter frame 225 and providing a seat against which valve leaflets 240 may close during diastole; and a perimeter seal 265 (preferably formed out of expanded Teflon or the like). Perimeter seal 265 acts like a step to help support valve leaflets 240 during diastole.

In addition, it should also be appreciated that soft outer cuff 235 may comprise a radially expandable mechanism (e.g., a balloon, a decompressed sponge, a spring loaded leaflet, etc.) for sealing deployable valve/filter apparatus 205 against the inner wall of vascular structure 222.

FIGS. 5A–5D illustrate operation of deployable valve/filter apparatus 205 of FIGS. 4A and 4B. More particularly, valve/filter apparatus 205 is first inserted through a small incision 270 in the wall of the vascular structure 222 (see FIG. 5A). Then deployable valve/filter frame 225 is deployed (see FIG. 5B). Thereafter, during systole (see FIG. 5C), blood flows through deployable valve/filter frame 225, forcing valve leaflets 240 open, and proceeds through filter bag 230. Any debris contained in the blood is captured by filter bag 230 and thereby prevented from moving downstream past valve/filter apparatus 205. During diastole (see FIG. 5D), when the blood flow momentarily reverses direction, valve leaflets 240 (shown in FIGS. 4A and 4B) close, seating against co-aptation strands 260 (shown in FIGS. 4A and 4B) across the interior of deployable valve/filter frame 225 (shown in FIGS. 4A and 4B). The closed leaflets 240 (shown in FIGS. 4A and 4B) prevent blood from passing back through the valve/filter frame 225 (shown in FIGS. 4A and 4B).

It should also be appreciated that with valve/filter apparatus 205 shown in FIGS. 4A, 4B and 5A–5D, valve leaflets 240 may be attached to structures other than center post 250, e.g., they may be attached to co-aptation strands 260, or to deployable valve filter frame 225, etc. Furthermore, if desired, valve leaflets 240 may be biased closed, or biased open. In addition, valve entrapment mechanism 215 may consist of one or more flaps (not shown), and have a configuration including, but not limited to, a single disk diaphragm (not shown), a semi-lunar configuration (not shown), a gill slit configuration (not shown), a multi-leaflet flap configuration (not shown), etc.

Figure 6A:
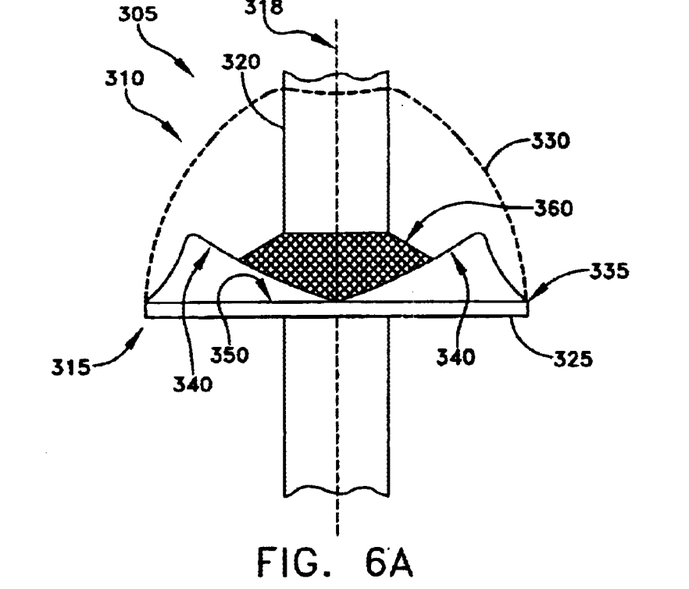
FIGS. 6A–6D are schematic illustrations depicting an orthogonally deployable valve/filter apparatus.
Figure 6B:
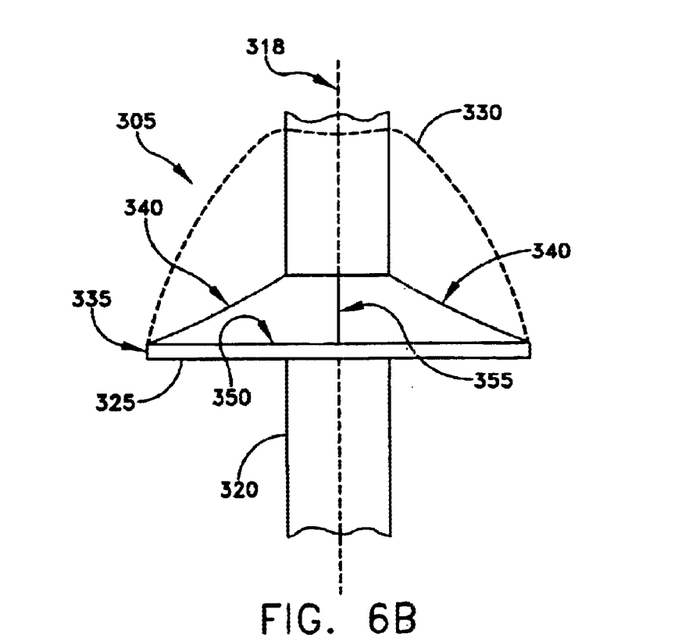
Figure 6C:
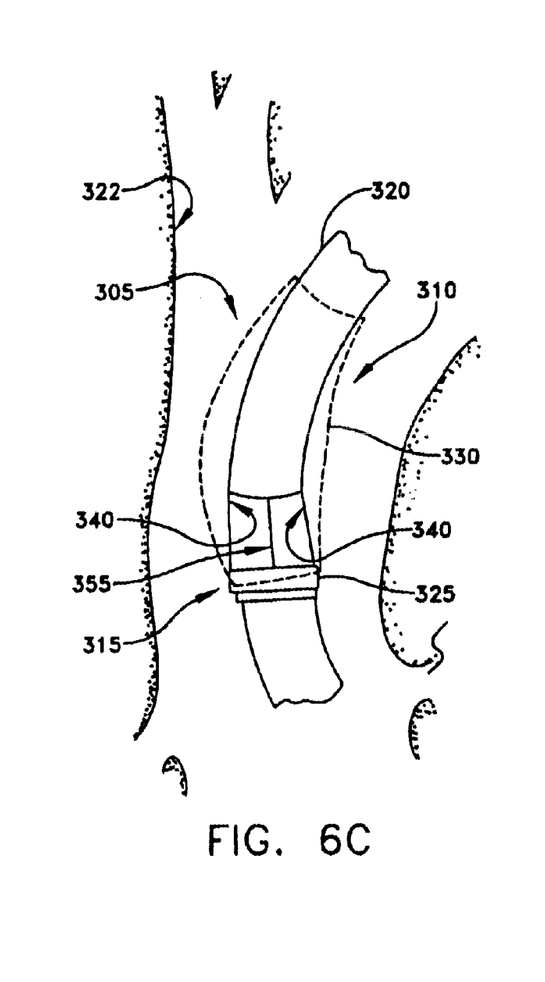
Figure 6D:
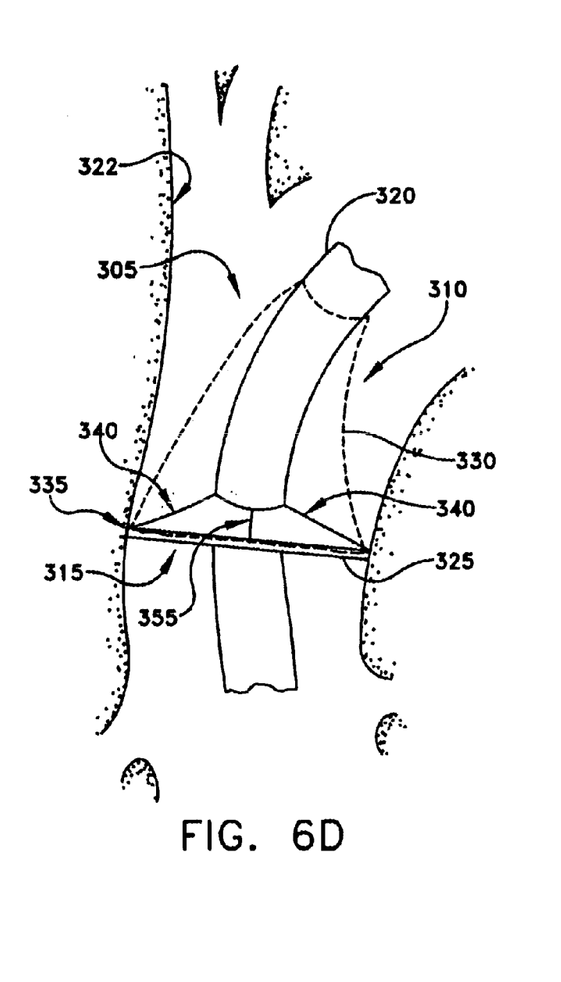

Looking next at FIGS. 6A–6B, there is shown an orthogonally deployable valve/filter apparatus 305. Orthogonally deployable valve/filter apparatus 305 of FIGS. 6A–6D generally comprises a filter device 310 and a valve entrapment mechanism 315 deployed at an angle substantially orthogonal to an axis 318 of a cannula 320, such as a catheter introduced to the vascular system at a location which may be remote from the point of operation, in the interior of a vascular structure 322; a deployable valve/filter frame 325; a filter bag 330 attached to the perimeter of deployable valve/filter frame 325; a compliant, soft outer cuff 335 (preferably formed out of a biologically inert material such as Teflon, Dacron, Silastic, etc.) for sealing the filter device 310 against the inner wall of vascular structure 322 when deployable valve/filter frame 325 is expanded; valve leaflets 340, preferably in the form of a blood-impervious material, having a first portion 350 in attachment to deployable valve/filter frame 325, and a second portion 355 separable from deployable valve/filter frame 325, so as to allow valve leaflets 340 to open and close; and a mesh material 360 extending across the interior of deployable valve/filter frame 325 and providing a seat against which valve leaflets 340 may close during diastole. In addition, it should be appreciated that mesh material 360 may comprise coaptation strands such as coaptation strands 160 as first shown in FIG. 2A.

In addition, it should also be appreciated that soft outer cuff 335 may comprise a radially expandable mechanism (e.g., a balloon, a decompressed sponge, a spring loaded leaflet, etc.) for sealing orthogonally deployable valve/filter apparatus 305 against the inner wall of vascular structure 322.

In addition, it should also be appreciated that valve entrapment mechanism 315 may be mounted for blood flow in either direction within vascular structure 322. FIGS. 6A–6D illustrate operation of deployable valve/filter apparatus 305. More particularly, deployable valve/filter apparatus 305 is first inserted through the interior of vascular structure 322 to a desired location (see FIG. 6C). Then deployable valve/filter frame 325 is deployed (see FIG. 6D) Thereafter, during systole (see FIG. 6A), blood flows through deployable valve/filter frame 325, forcing valve leaflets 340 open, and proceeds through filter bag 330. Any debris contained in the blood is captured by filter bag 330 and thereby prevented from moving downstream past deployable valve/filter apparatus 305. During diastole (see FIG. 6B), when the blood flow momentarily reverses direction, valve leaflets 340 close, seating against mesh material 360 across the interior of deployable filter frame 325. The closed leaflets 340 prevent blood from passing back through the valve/filter frame 325.

It should also be appreciated that with valve/filter apparatus 305 shown in FIGS. 6A–6D, valve leaflets 340 may be attached to structures other than deployable valve/filter frame 325, e.g., they may be attached to mesh material 360, or to cannula 320, etc. Furthermore, if desired, valve leaflets 340 may be biased closed, or biased open. In addition, valve entrapment mechanism 315 may consist of one or more flaps (not shown), and have a configuration including, but not limited to, a single disk diaphragm (not shown), a semi-lunar configuration (not shown), a gill slit configuration (not shown), a multi-leaflet flap configuration (not shown), etc.

The filter design as described herein to prevent the escape of captured debris during diastole or filter removal may also be applied to all intravascular filters. Such a filter design may comprise a one-way valve and a filtering mesh in series. Liberated debris may pass through the one-way valve and come to rest in the filtering mesh. The one-way valve ensures permanent entrapment of debris. Potential applications of such an apparatus extend to all percutaneous and surgical procedures on the heart and vascular system, including open heart surgery, balloon dilatation of cardiac valves and arteries, deployment of stents in arteries, diagnostic catheterizations, and other cardiac and vascular procedures. Advantages of such a system include more complete collection of liberated debris, with a resulting decrease in the complications attributable to such debris.

What is claimed is:

1. Apparatus for filtering and entrapping debris in the vascular system of a patient, said apparatus comprising:
   a filter device adapted to allow blood flow therethrough and to restrict passage of debris therethrough, said filter device having, a proximal side and a distal side, said filter device being adapted to capture debris carried in a first direction of blood flow from the proximal side to the distal side thereof on the proximal side of said filter device;
   an entrapment device having a proximal side and a distal side, said entrapment device comprising flap means on the distal side thereof adapted to open to allow passage of debris and blood therethrough in the first direction of blood flow from the proximal side to the distal side of said entrapment device, said flap means being operable to close to prevent debris passage from the distal side to the proximal side of said entrapment device in a second direction opposite to the first direction, said filter device and said entrapment device forming a chamber therebetween; and
   said apparatus being deployable within the vascular system;
   wherein said entrapment device allows blood and debris carried therein to flow therethrough in the first direction of blood flow and said filter device allows blood to flow therethrough in the first direction of blood flow, and said entrapment device flap means prevent debris from flowing back therethrough in the second direction of blood flow opposite to the first direction of blood flow such that the debris is trapped within the chamber for removal from the vascular system of the patient.

2. Apparatus according to claim 1 further comprising an introduction mechanism including a cannula to insert said apparatus into the vascular system of the patient.

3. Apparatus according to claim 1 further comprising a frame selectively configurable to adjustably size said filter device and said entrapment device.

4. Apparatus according to claim 3 further comprising a compliant outer cuff configured to surround said frame, and to make contact with an inner wall of the vascular system of the patient.

5. Apparatus according to claim 4 wherein said compliant outer cuff passively surrounds said frame.

6. Apparatus according to claim 4 wherein said compliant outer cuff is radially expandable.

7. Apparatus according to claim 1 wherein said filter device comprises a filter bag.

8. Apparatus according to claim 1 wherein said entrapment device flap means comprise at least one entrapment leaflet attached to a first portion of said entrapment device on the distal side of said entrapment device and contacting a second portion of said entrapment device on the distal side of said entrapment device such that said at least one entrapment leaflet is moveable to a position removed from the second distal side of said entrapment device to allow blood and debris in the first direction of blood flow therethrough and said at least one entrapment leaflet is moveable toward the second distal side of said entrapment device to prevent debris flow in the second direction of blood flow therethrough.

9. Apparatus according to claim 8 wherein said at least one entrapment leaflet comprises a filter material so as to allow flow of blood, and to prevent flow of debris, in the second direction of blood flow back through said entrapment device.

10. Apparatus according to claim 8 wherein said at least one entrapment leaflet comprises a non-porous material so as to prevent blood and debris flow in the second direction of blood flow back through said entrapment device.

11. Apparatus according to claim 1 wherein the first direction of blood flow is the direction of systolic blood flow and the second direction of blood flow is the direction of diastolic blood flow.

12. A method for filtering and entrapping debris from the vascular system of a patient, the method comprising:

providing apparatus for filtering and entrapping debris in the vascular system of a patient, the apparatus comprising:

a filter device adapted to allow blood flow therethrough and to restrict passage of debris therethrough, the filter device having a proximal side and a distal side, the filter device being adapted to capture debris carried in a first direction of blood flow from the proximal side to the distal side thereof on the proximal side of the filter device;

an entrapment device having a proximal side and a distal side, the entrapment device comprising flaps means on the distal side thereof adapted to open to allow passage of blood and debris therethrough in the first direction of blood flow from the proximal side to the distal side of the entrapment device, the flap means being operable to close to prevent debris passage from the distal side to the proximal side of the entrapment device in a second direction opposite to the first direction, the filter device and the entrapment device forming a chamber therebetween; and the apparatus being deployable within the vascular system;

wherein the entrapment device allows blood and debris carried therein to flow therethrough in the first direction of blood flow and the filter device allows blood to flow therethrough in the first direction of blood flow, and the entrapment device prevents debris from flowing back therethrough in the second direction of blood flow opposite to the first direction of blood flow such that the flap means entrap the filtered debris within the chamber for removal from the vascular system of the patient;

inserting the apparatus into the vascular system of the patient; and allowing blood and debris carried therein to flow through the entrapment device, and into the chamber.

13. A method according to claim 12 further comprising the step of making an opening in a wall of a portion of the vascular system prior to the step of inserting the apparatus into the vascular system of the patient wherein the apparatus is inserted through the opening.

14. A method according to claim 13 wherein the portion is the aorta of the patient.

15. A method according to claim 12 further comprising the step of removing the apparatus from the vascular system of the patient.

16. A method according to claim 12 wherein the apparatus maintains entrapment of debris during the step of removing the apparatus from the vascular system of the patient.

17. An apparatus for filtering and entrapping debris in a vascular system of a patient, the apparatus comprising:

an entrapment device comprising an annular member;

flap means fixed to said annular member and extending toward a center of said annular member, said flap means being moveable by flood flow in a first direction through said annular member to provide a central orifice for blood and debris therein to flow therethrough; and a filter bag fixed at an open end thereof to said annular member and adapted to permit blood flow therethrough in the first direction and collect the debris flowed thereinto;

wherein upon reversal of the direction of blood flow, said filter bag permits blood flow therethrough, and said flap means is moveable by the blood flow to close the orifice to prevent flow of debris in a direction opposite to the first direction.

* * * * *